(12) United States Patent
Bai et al.

(10) Patent No.: US 8,940,086 B2
(45) Date of Patent: Jan. 27, 2015

(54) PROCESS OF MAKING ANTIBACTERIAL COATING AND ANTIBACTERIAL PAPER WITH SAME, AND ANTIBACTERIAL PAPER

(71) Applicant: Ningbo Asia Pulp & Paper Co., Ltd, Ningbo (CN)

(72) Inventors: Shu-Hua Bai, Taichang (TW); Jun-Ming Wang, Ningbo (CN); Ji-Ping Quan, Ningbo (CN); Meng-Huai Ran, Ningbo (CN); Wei He, Ningbo (CN)

(73) Assignee: Ningbo Asia Pulp & Paper Co., Ltd, Ningbo, Zhejiang Province (CN)

( * ) Notice: Subject to any disclaimer, the term of this patent is extended or adjusted under 35 U.S.C. 154(b) by 0 days.

(21) Appl. No.: 14/093,027

(22) Filed: Nov. 28, 2013

(65) Prior Publication Data

US 2014/0083635 A1      Mar. 27, 2014

Related U.S. Application Data

(63) Continuation of application No. PCT/CN2013/000370, filed on Mar. 31, 2013.

(30) Foreign Application Priority Data

Mar. 31, 2012 (CN) .......................... 2012 1 0095148

(51) Int. Cl.
| | |
|---|---|
| *C09D 5/14* | (2006.01) |
| *D21H 21/36* | (2006.01) |
| *D21H 21/52* | (2006.01) |
| *C09D 5/16* | (2006.01) |
| *C09D 7/12* | (2006.01) |
| *D21H 19/12* | (2006.01) |
| *D21H 19/38* | (2006.01) |
| *C08K 3/22* | (2006.01) |

(52) U.S. Cl.
CPC .................. *C09D 5/14* (2013.01); *D21H 21/36* (2013.01); *D21H 21/52* (2013.01); *C09D 5/1618* (2013.01); *C09D 7/1266* (2013.01); *C09D 7/1275* (2013.01); *D21H 19/12* (2013.01); *D21H 19/38* (2013.01); *C08K 2003/2241* (2013.01)
USPC ........................................ 106/15.05; 162/161

(58) Field of Classification Search
USPC ........................................ 106/15.05; 162/161
See application file for complete search history.

(56) References Cited

U.S. PATENT DOCUMENTS

| | | | | |
|---|---|---|---|---|
| 8,636,974 | B2 * | 1/2014 | Enomura ....................... | 423/612 |
| 2006/0233697 | A1 * | 10/2006 | Zhou et al. ..................... | 423/610 |
| 2008/0108740 | A1 * | 5/2008 | Evers ............................. | 524/431 |
| 2009/0107362 | A1 * | 4/2009 | Tarng et al. ................... | 106/428 |
| 2009/0253853 | A1 * | 10/2009 | Lin et al. ....................... | 524/497 |
| 2014/0083635 | A1 * | 3/2014 | Bai et al. ....................... | 162/161 |

FOREIGN PATENT DOCUMENTS

DE    10 2010 041 290 A1 *    5/2011    ............. D21H 21/36

OTHER PUBLICATIONS

Derwent-Acc-No. 2008-H14771, abstract of Chinese Patent Specification No. CN 101153137 A (Apr. 2008).*
Derwent-Acc-No. 2012-B99656, abstract of Chinese Patent Specification No. CN 102329552 A (Jan. 2012).*
Derwent-Acc-No: 2013-E46417, abstract of Chinese Patent Specification No. CN 102826598 A (Dec. 2012).*
Derwent-Acc-No: 2013-T24782, abstract of Chinese Patent Specification No. CN 103194935 A (Jul. 2013).*

* cited by examiner

*Primary Examiner* — Anthony J Green
(74) *Attorney, Agent, or Firm* — Cheng-Ju Chiang

(57) ABSTRACT

Process for making an antibacterial coating includes the following steps. A solution containing titanium dioxide particles and a dispersant is prepared. A mechanical stirring method is employed to prepare a preliminary titanium dioxide dispersed solution. An ultrasonic agitation method is employed to prepare a nanometer titanium dioxide dispersed solution, an average particle size of the titanium dioxide particles being less than or equal to 200 nanometers. Lastly, the nanometer titanium dioxide dispersed solution is mixed with a paper-making coating to prepare an antibacterial coating.

8 Claims, 14 Drawing Sheets

Surface

Cross section

Surface

Cross section

Surface

Cross section

Surface

Cross section

Surface

Cross section

Surface

Cross section

Surface

Cross section

PROCESS OF MAKING ANTIBACTERIAL COATING AND ANTIBACTERIAL PAPER WITH SAME, AND ANTIBACTERIAL PAPER

CROSS-REFERENCE TO RELATED APPLICATION

This application is a continuation application of International Application No. PCT/CN2013/000370, which has an international filing date of Mar. 31, 2013.

BACKGROUND

1. Technical Field

The present disclosure relates to a process for making an antibacterial coating, and a process for making an antibacterial paper having the antibacterial coating.

2. Description of Related Art

Today, not only do people need tissue paper and industrial paper for hygiene and to keep things sterile, but they also need the paper itself to have antibacterial capability.

A conventional process of making an antibacterial paper involves coating an antibacterial layer containing nanometer-sized titanium dioxide particles on a paper surface, to make the paper have antibacterial capability. However, the antibacterial effect of the antibacterial paper made by this method is not as good as it would ideally be. The main reason is that the method cannot fully employ the antibacterial capability of the nanometer-sized titanium dioxide particles.

In the above-described process of making antibacterial paper, the nanometer-sized titanium dioxide particles used in the antibacterial layer are supplied by a supplier. It is well known that the antibacterial capability of the nanometer-sized titanium dioxide particles depends on the average particle size of the particles. In particular, the smaller the average particle size of the titanium dioxide particles is, the better antibacterial capability the titanium dioxide particles have. However, as the particle size of the titanium dioxide particles becomes smaller, the specific surface energy of the titanium dioxide particles becomes larger. The large specific surface energy causes nanometer-sized titanium dioxide particles to aggregate during storage or transportation. The aggregation of the titanium dioxide particles greatly increases the average size of the titanium dioxide particles. As a result, the antibacterial capability of the nanometer-sized titanium dioxide particles is reduced.

Therefore, a process of making an antibacterial coating and a process of making an antibacterial paper using the antibacterial coating to overcome the above-mentioned problems are needed.

DETAILED DESCRIPTION

Figure 1A:
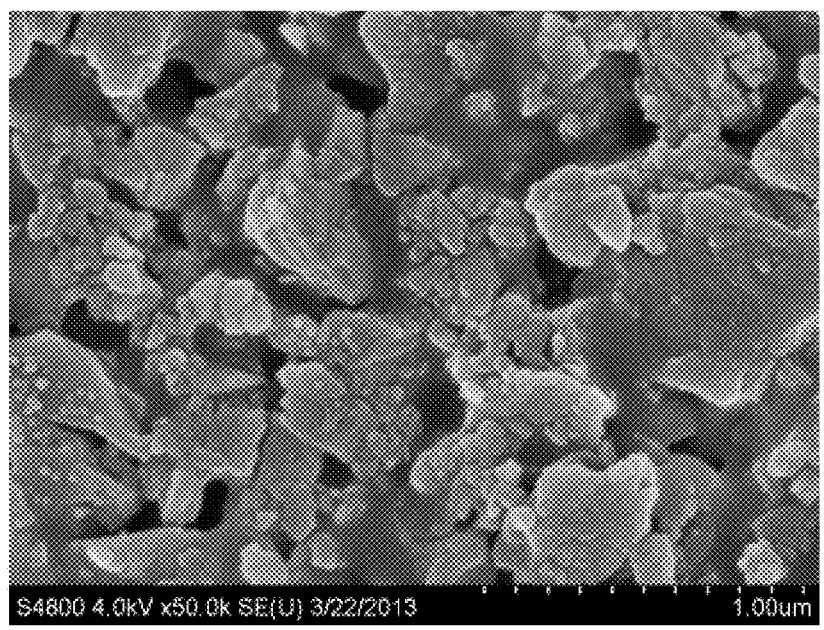
FIG. 1A and FIG. 1B respectively shows superficial and cross-sectional electron micrographs of an antibacterial coating layer formed by an antibacterial coating prepared by mechanical stirring with a speed of 5000 rpm (revolutions per minute) in a comparative example 1 of the present disclosure.
Figure 1B:
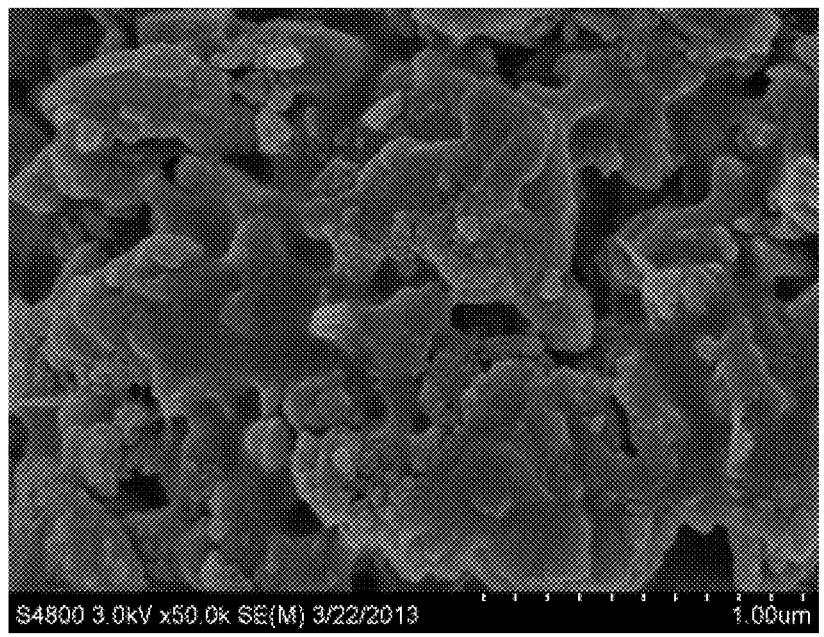
Figure 2A:
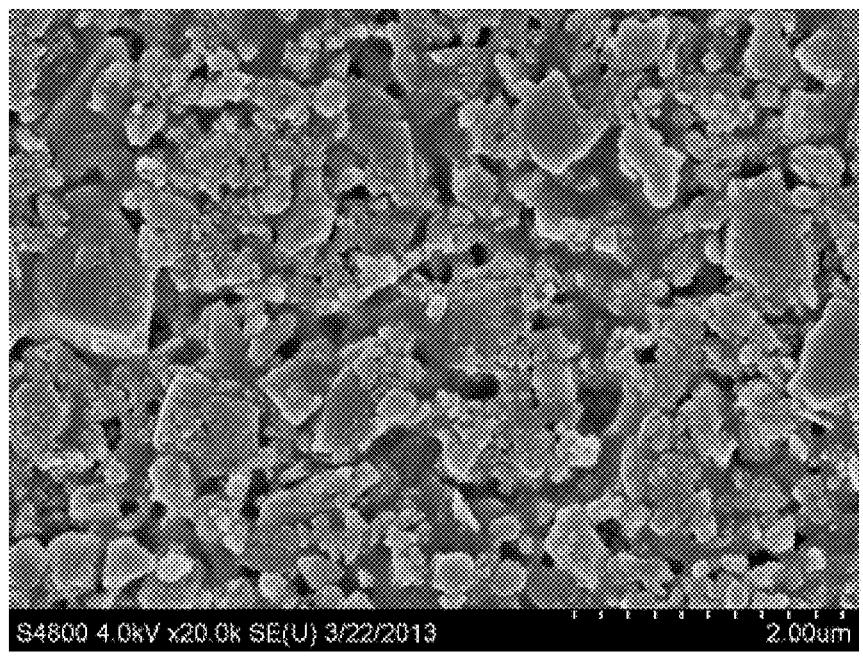
FIG. 2A and FIG. 2B respectively shows superficial and cross-sectional electron micrographs of an antibacterial coating layer formed by an antibacterial coating prepared by mechanical stirring with a speed of 6000 rpm in the comparative example 1 of the present disclosure.
Figure 2B:
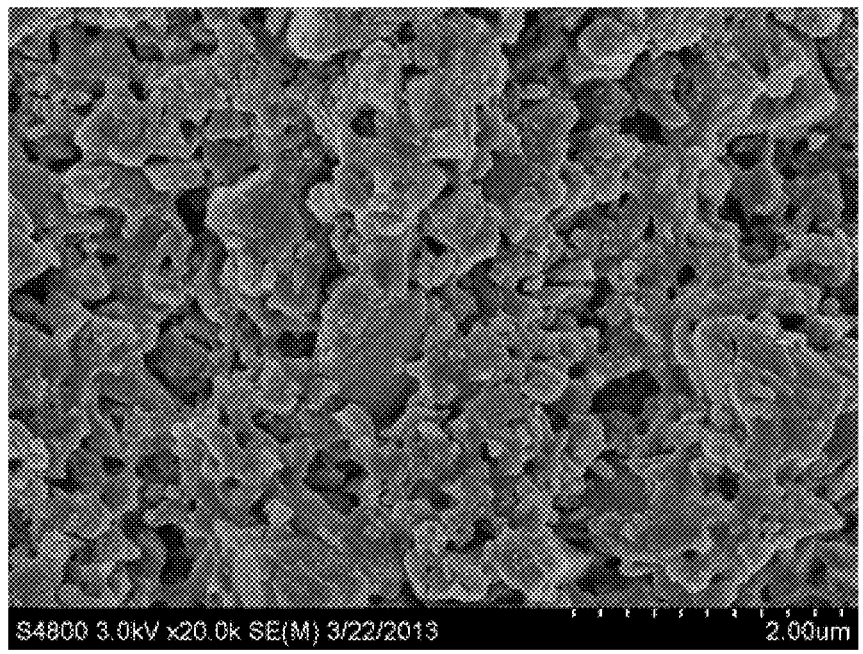
Figure 3A:
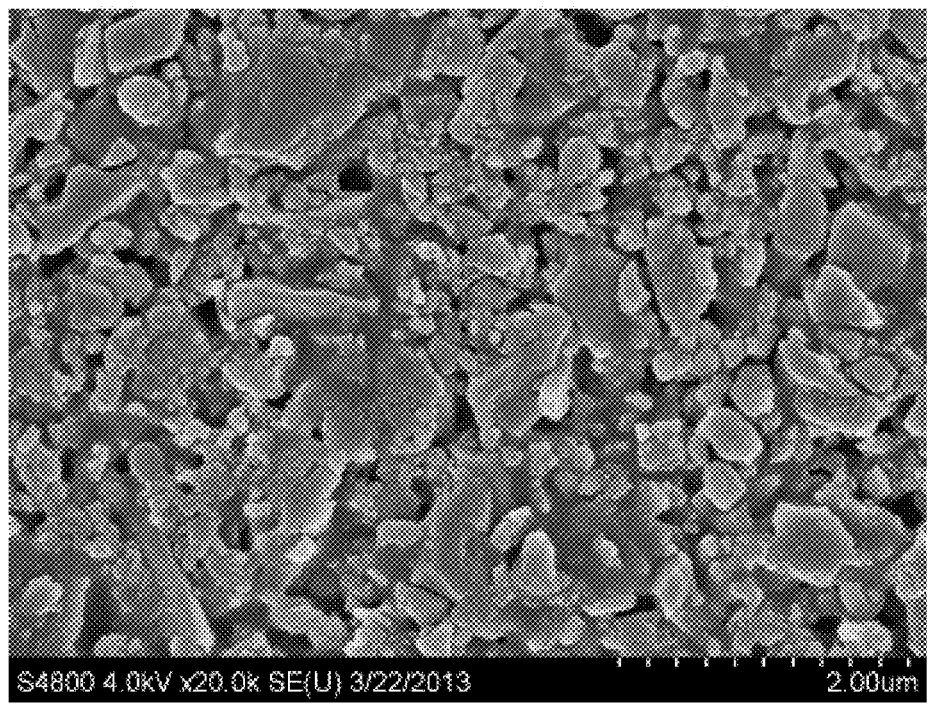
FIG. 3A and FIG. 3B respectively shows superficial and cross-sectional electron micrographs of an antibacterial coating layer formed by an antibacterial coating prepared by mechanical stirring with a speed of 7000 rpm in the comparative example 1 of the present disclosure.
Figure 3B:
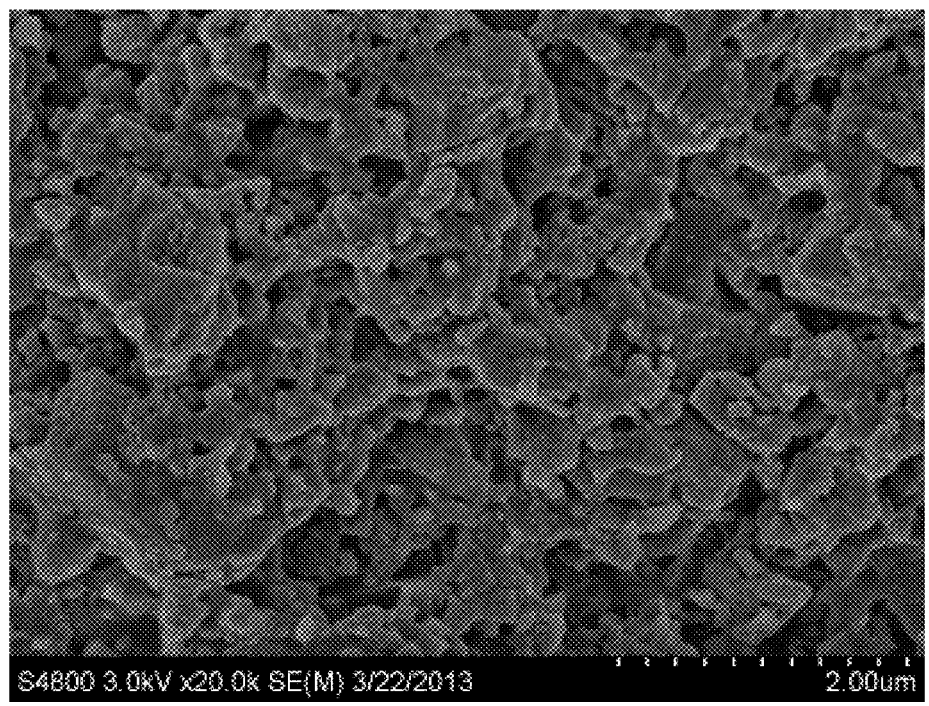
Figure 4A:
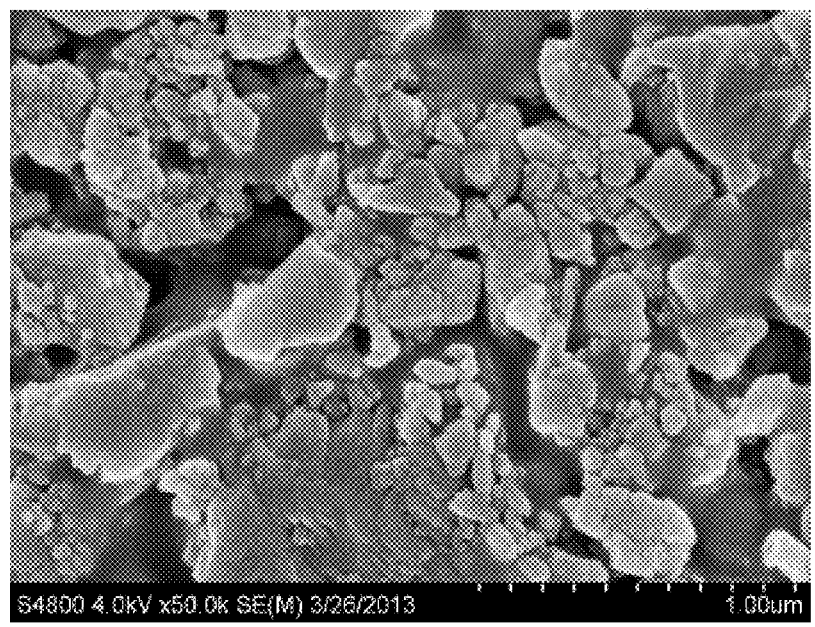
FIG. 4A and FIG. 4B respectively shows superficial and cross-sectional electron micrographs of an antibacterial coating layer formed by an antibacterial coating prepared by ultrasonic agitation for 3 mins (minutes) in a comparative example 2 of the present disclosure.
Figure 4B:
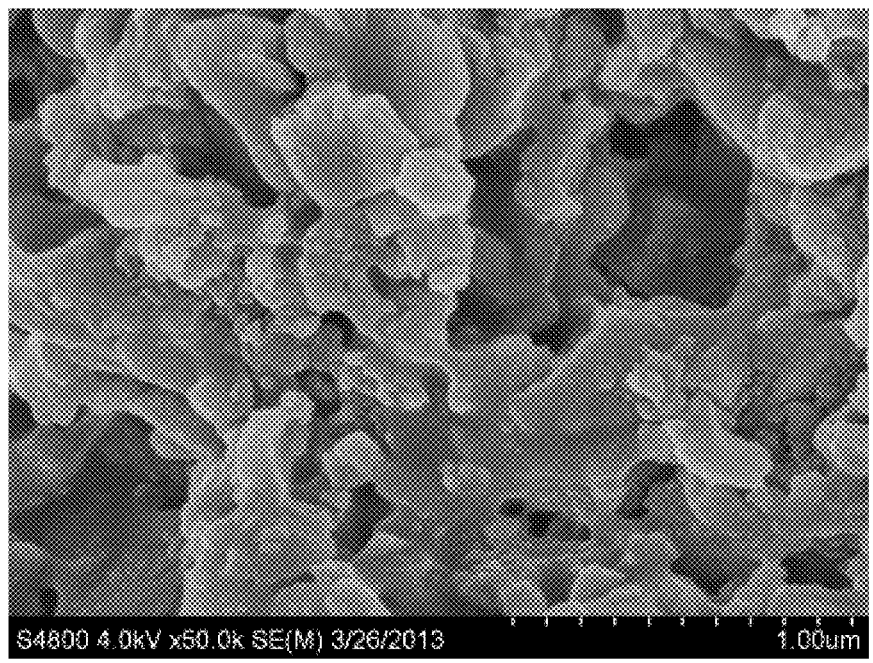
Figure 5A:
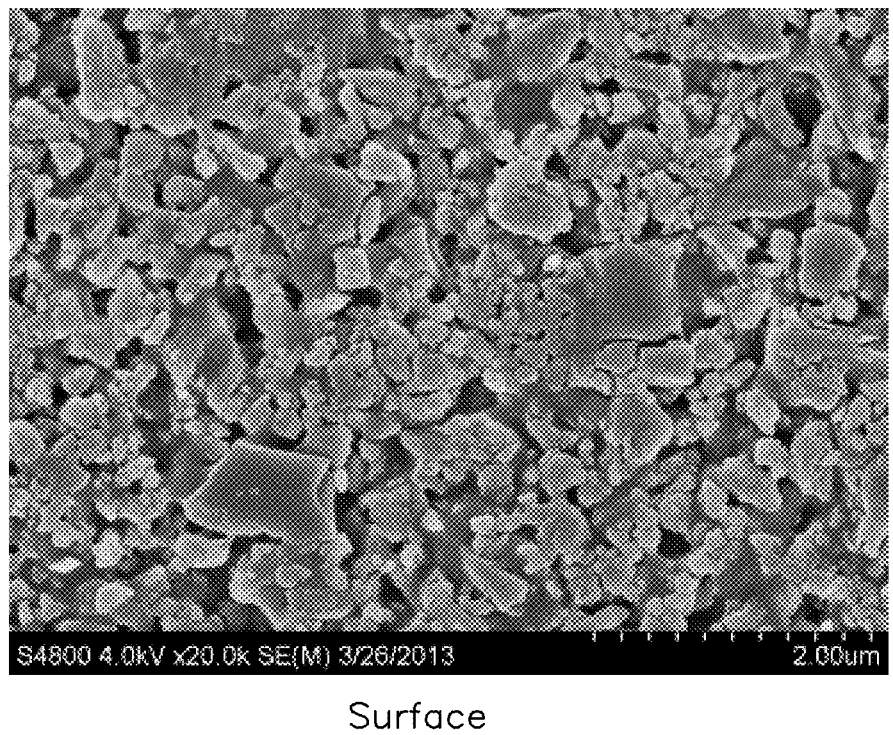
FIG. 5A and FIG. 5B respectively shows superficial and cross-sectional electron micrographs of an antibacterial coating layer formed by an antibacterial coating prepared by ultrasonic agitation for 4 mins in the comparative example 2 of the present disclosure.
Figure 5B:
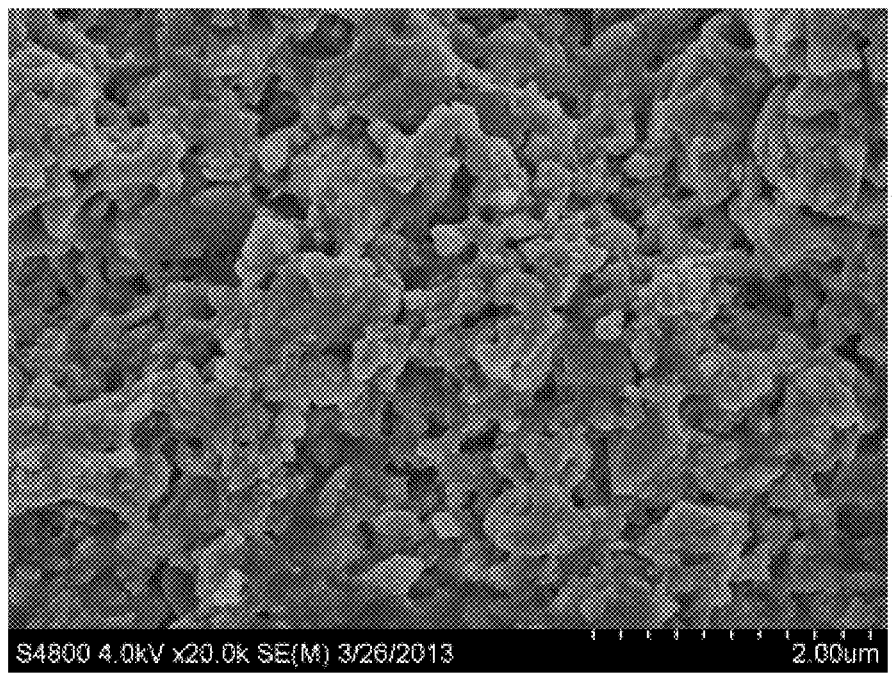
Figure 6A:
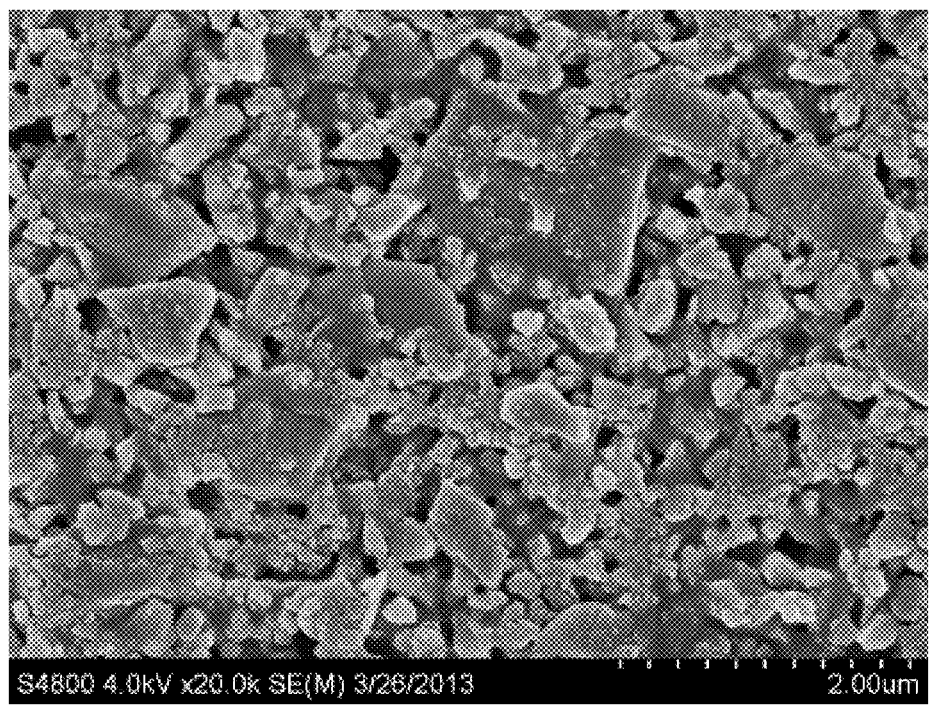
FIG. 6A and FIG. 6B respectively shows superficial and cross-sectional electron micrographs of an antibacterial coating layer formed by an antibacterial coating prepared by ultrasonic agitation for 5 mins in the comparative example 2 of the present disclosure.
Figure 6B:
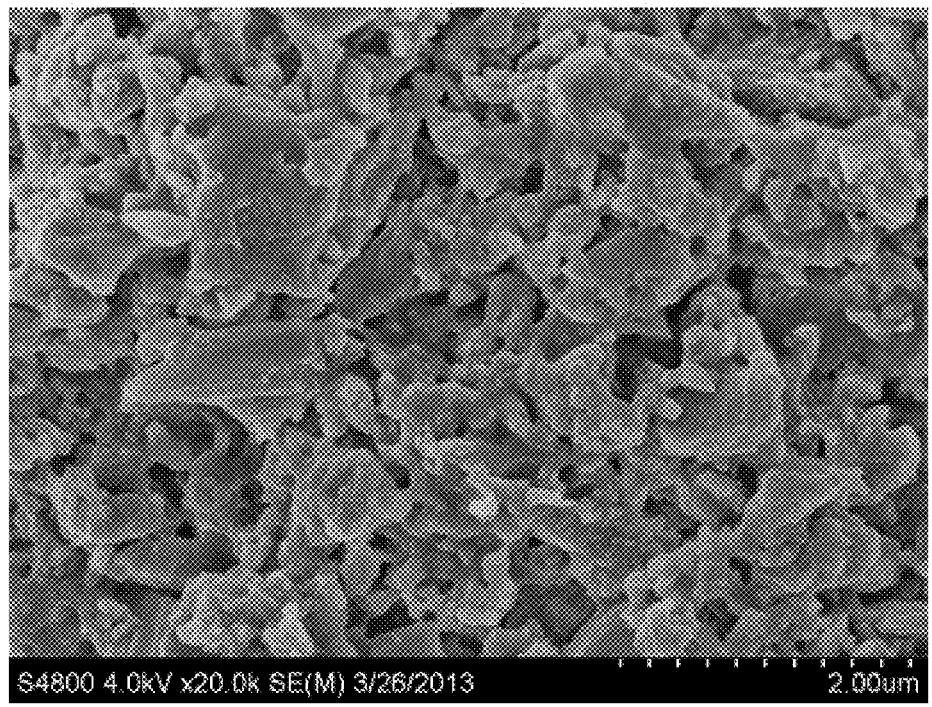

In a first embodiment, the present disclosure provides a process of making an antibacterial coating. In the following description, where the context permits, a "coating" includes a reference to a substance used for coating. The process includes the following steps:

Step 1: preparing a mixed solution containing titanium dioxide particles and a dispersant.

In this embodiment, the mixed solution is prepared by the following steps: (a) adjusting the pH value of water to be greater than 7; (b) adding the dispersant into the water while stirring to obtain a dispersant solution; and (c) adding the titanium dioxide particles into the dispersant solution to obtain the mixed solution. In the present embodiment, in step (a), the pH value can be maintained in the range of from about 9 to about 10 by adding an alkaline substance.

In step (a), the alkaline substance can be sodium hydroxide (NaOH), sodium carbonate ($Na_2CO_3$), or other alkaline substance commonly used in the art. The dispersant can be a sodium polyacrylate (PAAS), a cetyltrimethylammonium bromide (CTAB), a sodium hexametaphosphate (SHMP), a polyethylene glycol-2000 (PEG-2000, wherein the relative molecular mass of the PEG is about 2000), a polymethacrylic acid (PMAA), or other dispersant commonly used in the art.

In step (c), the titanium dioxide particles added into the dispersant solution are a commercially available finished product. The finished titanium dioxide particles can be nano-treated titanium dioxide particles or ordinary untreated titanium dioxide particles.

In this embodiment, the employed titanium dioxide particles are nano-treated titanium dioxide particles. Referring also to the above description in the Related Art section of this disclosure, although the titanium dioxide particles have been nano-treated, the actual average particle size of the titanium dioxide particles employed by a typical papermaking factory is above 1000 nanometers (nm), due to aggregation between particles during storage and transportation. Such average particle size is far beyond the acceptable range for nanometer-level purposes.

It is to be understood that in this embodiment, the pH value of the mixed solution is not limited to the range of from about 9 to about 10, and can be adjusted according to the situation on the condition that such adjustment does not adversely affect the performance of the antibacterial coating.

It should be noted that, the pH value of the mixed solution is not a key factor that must be considered in the process of making the antibacterial coating. In this embodiment, the reason for maintaining the pH value of the mixed solution as alkaline is that the pH value of a papermaking coating system employing the present process is alkaline. Therefore, keeping the pH value of the mixed solution as alkaline can avoid a possible negative effect caused by inconsistencies between the pH of the mixed solution and the pH of the papermaking coating system.

It is to be understood that in the present disclosure, the mixed solution containing titanium dioxide particles in a dispersant can be prepared according to the following situations: (i) when the pH value of the papermaking coating system is alkaline, the mixed solution may be prepared under alkaline conditions, or adjusted to an alkaline state after the mixed solution is prepared under acidic or neutral conditions; (ii) when the pH value of the papermaking coating system is acidic, the mixed solution may be prepared under acidic conditions, or adjusted to an acidic state after the mixed solution is prepared under alkaline or neutral conditions; and (iii) when the pH value of the papermaking coating system is neutral, the mixed solution may be prepared under neutral conditions or adjusted to a neutral state after the mixed solution is prepared under alkaline or acidic conditions.

In the present disclosure, the mass percentage of the dispersant contained in the mixed solution depends on the mass percentage of the titanium dioxide particles contained in the mixed solution. In this embodiment, the mass percentage of the dispersant contained in the mixed solution is in the range of from about 0.3% to about 0.5% of the mass of the titanium dioxide particles contained in the mixed solution. It is to be understood that the mass percentage of the titanium dioxide particles contained in the mixed solution is not limited to the above-mentioned range, and can be adjust according to the situation on the condition that the adjustment does not adversely affect the dispersion effect of the mixed solution.

It is to be understood that in the present disclosure, when preparing the mixed solution, the order of adding the dispersant and the titanium dioxide particles is not limited to the above-described order. For example, in steps (b) and (c), the dispersant and titanium dioxide particles can be added into the water at the same time, the dispersant can be added into the water before the titanium dioxide particles, or the titanium dioxide particles can be added into the water before the dispersant.

Step 2: primary beating and breaking up of the titanium dioxide particles in the mixed solution by way of mechanical stirring to decrease the average particle size of the titanium dioxide particles and prepare a preliminary titanium dioxide dispersed solution.

In this embodiment, the stirring speed of the mechanical stirring is in the range of from about 5000 to about 7000 revolutions per minute (rpm), and the stirring time of the mechanical stirring is in the range of from about 30 to about 60 minutes. It is to be understood that in the present disclosure, the stirring speed and the stirring time of the mechanical stirring also can be changed according to the original average particle size of the titanium dioxide particles added in the mixed solution. When the titanium dioxide particles added into the mixed solution are the untreated titanium dioxide particles, the stirring speed may be higher, and the stirring time may be longer. When the titanium dioxide particles added into the mixed solution are the nano-treated titanium dioxide particles, the stirring speed may be lower, and the stirring time may be shorter for saving energy.

Step 3: further beating and breaking up the titanium dioxide particles in the preliminary titanium dioxide dispersed solution by way of ultrasonic agitation to further decrease the average particle size of the titanium dioxide particles and thus prepare a titanium dioxide dispersed solution with an average particle size of the titanium dioxide particles being less than or equal to about 200 nanometers.

In this embodiment, the ultrasonic power is 500 W (watts), the ultrasonic frequency is in the range of from about 10 to about 100 kHz (kilohertz), and the time of ultrasonic agitation is in the range of from about 3 to about 5 minutes. It is to be understood that in the present disclosure, the ultrasonic power, the ultrasonic frequency, and the time of ultrasonic agitation can be adjusted according to the situation as long as the average particle size of the titanium dioxide particles is reduced to about 200 nanometers or less.

In the present disclosure, the reason for firstly employing the mechanical stirring method to beat and break up the titanium dioxide particles is that the mechanical stirring method quickly and effectively decreases the average particle size of the titanium dioxide particles when the average particle size of the titanium dioxide particles is larger than about 800 nanometers. When the average particle size of the titanium dioxide particles is less than about 800 nanometers, the beating effect of the mechanical stirring is weak. Accordingly, the ultrasonic agitation method is employed to effectively decrease the average particle size of the titanium dioxide particles and obtain nanometer-sized titanium dioxide particles with the average particle size being less than or equal to 200 nanometers.

The method of combining the mechanical stirring and the ultrasonic agitation employed in the present disclosure as opposed to just employing the ultrasonic agitation method to break up the titanium dioxide particles has the following advantages. First, compared to the ultrasonic agitation method, the energy consumption of the mechanical stirring method is lower. When the average particle size of the titanium dioxide particles is larger, only employing the ultrasonic agitation method to beat and break up the titanium dioxide particles consumes a lot of energy and obviously increases the cost of papermaking. In the present disclosure, the approach of firstly employing the mechanical stirring method to beat and break up the titanium dioxide particles to make the average particle size of the titanium dioxide particles smaller and then employing the ultrasonic agitation method to further beat and break up the smaller titanium dioxide particles to obtain the nanometer-sized titanium dioxide particles with the average particle size being less than or equal to 200 nanometers can effectively decrease the energy required for making nanometer-sized titanium dioxide particles and thus reduce the cost of papermaking. Second, the ultrasonic agitation method effectively breaks up the smaller titanium dioxide particles by generating shock waves to make the titanium dioxide particles violently impact each other. By comparison, for the larger titanium dioxide particles, the impact effect caused by the shock waves is weak, and it is difficult to effectively break down the titanium dioxide particles to the nanometer level. Therefore in the present disclosure, firstly employing the mechanical stirring method to effectively break down the larger titanium dioxide particles helps the shock waves generated by the ultrasonic agitation method effectively break down the titanium dioxide particles to the nanometer size.

Step 4: mixing the nanometer-sized titanium dioxide dispersed solution with a papermaking coating to prepare an antibacterial coating with the nanometer-sized titanium dioxide particles uniformly disperse therein. Typically, the mass percentage of the nanometer-sized titanium dioxide particles in the antibacterial coating is more than or equal to 5% of the mass of the antibacterial coating.

Before the nanometer-sized titanium dioxide dispersed solution is mixed with the papermaking coating, the nanometer-sized titanium dioxide particles are evenly suspended in the dispersed solution with the help of the dispersant. When the nanometer-sized titanium dioxide dispersed solution is mixed with the papermaking coating, the larger filler particles contained in the papermaking coating, such as calcium carbonate ($CaCO_3$) particles, position themselves between the nanometer-sized titanium dioxide particles, thus preventing the titanium dioxide particles from aggregating due to the steric effect of the filler particles and keeping the particle size of the titanium dioxide particles in the antibacterial coating maintained within the nanometer range.

It is to be understood that in this step, the papermaking coating used to mix with the nanometer-sized titanium dioxide particles dispersed solution is a common papermaking coating used in the papermaking process. The kind and the mass percentage of the papermaking coating used in the antibacterial coating can be adjusted according to actual needs of the paper product. The mass percentage of the nanometer-sized titanium dioxide particles in the antibacterial coating can also be adjusted according to actual needs of the paper product. In this embodiment, the mass percentage of the nanometer-sized titanium dioxide particles in the antibacterial coating is in the range of from about 5% to about 15% of the mass of the antibacterial coating.

In a second embodiment, the present disclosure provides a process of making antibacterial paper, which includes the following steps: (i) providing a paper substrate; (ii) preparing an antibacterial coating according to the method provided in the first embodiment of the present disclosure; and (iii) employing the antibacterial coating to form an antibacterial layer on at least one external surface of the paper substrate.

In this embodiment, the paper substrate is a multilayer paper including a surface layer, a sandwich layer, and a bottom layer. The antibacterial layer is formed on the surface layer and/or the bottom layer of the paper substrate. It is to be understood that in the present disclosure, the number of layers of the paper substrate can also be changed according to different product designs.

In a third embodiment, the present disclosure provides an antibacterial paper. The antibacterial paper includes a paper substrate and an antibacterial coating layer coating on at least one external surface of the paper substrate. The antibacterial coating layer is formed by the antibacterial coating prepared by the process provided in the first embodiment of the present disclosure.

It is to be understood that in the present disclosure, the antibacterial paper may be antibacterial paperboard or other type of paper, such as culture paper, packing paper, or industrial paper. According to the number of layers, the antibacterial paper may be monolayer paper, double layer paper, or multilayer paper.

In this embodiment, the average particle size of the nanometer-sized titanium dioxide particles in the antibacterial coating layer is less than or equal to 200 nanometers. Typically, the average particle size of the nanometer-sized titanium dioxide particles in the antibacterial coating layer is in the range of 30 to 200 nanometers.

In this embodiment, the antibacterial efficiency of the antibacterial coating layer of the antibacterial paper is greater than or equal to 99%. The mass percentage of the nanometer-sized titanium dioxide particles contained in the antibacterial coating layer of the antibacterial paper is greater than or equal to 5% of the mass of the antibacterial coating layer. Typically, the mass percentage of the nanometer-sized titanium dioxide particles contained in the antibacterial coating layer of the antibacterial paper is in the range of from about 5% to about 15% of the mass of the antibacterial coating layer. It is to be understood that in the present disclosure, the antibacterial efficiency of the antibacterial coating layer and the mass percentage of the nanometer-sized titanium dioxide particles contained in the antibacterial coating layer are not limited to the above-mentioned values and range, and can be adjusted according to the actual needs of the preparing process of the antibacterial coating.

Compared to common antibacterial paper, the antibacterial paper provided in the third embodiment of the present disclosure has the following advantages: (i) because the average particle size of the nanometer-sized titanium dioxide particles contained in the antibacterial coating layer is less than or equal to 200 nanometers, the antibacterial capability of the nanometer-sized titanium dioxide particles is fully employed, giving good antibacterial capability to the antibacterial paper; and (ii) because the nanometer-sized titanium dioxide particles are uniformly distributed in the antibacterial coating layer due to the steric effect of the larger filler particles contained in the antibacterial coating, the antibacterial coating layer has high porosity on the external surface of the antibacterial paper. The high porosity improves the printing performance of the paper. Thus the antibacterial paper provided by the third embodiment of the present disclosure not only has high antibacterial efficiency, but also has good printing performance.

INTRODUCTION TO EXAMPLES

To further verify the antibacterial capability and the printing performance of the antibacterial paper provided by the present disclosure, three sets of examples are provided in the following description. In the three sets of examples, the materials and the process parameters used in the examples are the same, except for the method of beating and breaking up the titanium dioxide finished product supplied by the titanium dioxide supplier.

Comparative Example 1

In comparative example 1, only the mechanical stirring method is employed to beat and break up the titanium dioxide finished product supplied by the titanium dioxide supplier during the process of preparing an antibacterial coating. Then the antibacterial coating is employed to form an antibacterial coating layer on the external surface of a paper substrate to prepare an antibacterial paper. The specific steps include the following:

(i) preparing a papermaking pulp employing the following processes in this order: beating pulp, screening the pulp, cleaning the pulp, floating the pulp, heat-dispersing the pulp, bleaching the pulp, and refining the pulp;

(ii) employing the papermaking pulp to make the paper substrates;

(iii) preparing a papermaking coating;

(iv) preparing a titanium dioxide dispersed solution according to the following steps: (a) adding NaOH into water to adjust the pH value of the water to 9, adding a dispersant into the water with a mass percentage of the dispersant being 0.3% by mass of the titanium dioxide to be added, and stirring the water containing the dispersant with a rotational speed of 500 rpm to obtain a dispersant solution; (b) adding nano-treated titanium dioxide particles into the dispersant solution to obtain a mixed solution, wherein a mass percentage of the titanium dioxide particles in the mixed solution is 20% by mass of the mixed solution; and (c) employing three equal mass mixed solution samples from the mixed solution, mechanically stirring the three mixed solution samples 30 minutes with a rotational speed of 5000 rpm, 6000 rpm, and 7000 rpm, respectively, to obtain three titanium dioxide dispersed solutions, wherein the average particle size of the titanium dioxide particles in the three titanium dioxide dispersed solutions are shown in table 1 below;

(v) respectively mixing the three titanium dioxide dispersed solutions, obtained by the different mechanical stirring speeds, with the papermaking coating to obtain three equal mass antibacterial coatings, wherein in each antibacterial coating, the mass percentage of the titanium dioxide is 5% of the mass of the antibacterial coating; and (vi) employing three paper substrates made in step (ii), employing the three antibacterial coatings respectively to form antibacterial coating layers on the external surfaces of the three paper substrates to obtain three antibacterial papers, and employing an electron microscope to detect the superficial and cross-sectional structures of the antibacterial coating layer respectively formed on the external surface of the three antibacterial papers. The results are shown in FIGS. 1A~3B.

Comparative Example 2

Only employing the ultrasonic agitation method to beat and break up the titanium dioxide finished product supplied by the titanium dioxide supplier during the process of preparing an antibacterial coating, and then employing the antibacterial coating to form an antibacterial coating layer on the external surface of a paper substrate to prepare an antibacterial paper. The specific steps include the following:

(i) preparing a papermaking pulp employing the following processes in this order: beating pulp, screening the pulp, cleaning the pulp, floating the pulp, heat-dispersing the pulp, bleaching the pulp, and refining the pulp;

(ii) employing the papermaking pulp to make the paper substrates;

(iii) preparing a papermaking coating;

(iv) preparing a titanium dioxide dispersed solution according to the following steps: (a) adding NaOH into water to adjust the pH value of the water to 9, adding a dispersant into the water with a mass percentage of the dispersant being 0.3% by mass of the titanium dioxide to be added, and stirring the water containing the dispersant with a rotational speed of 500 rpm to obtain a dispersant solution; (b) adding nano-treated titanium dioxide particles into the dispersant solution to obtain a mixed solution, wherein a mass percentage of the titanium dioxide particles in the mixed solution is 20% of the mass of the mixed solution; and (c) employing three equal mass mixed solution samples from the mixed solution, respectively employing ultrasonic agitation to stir the three mixed solution samples 3 minutes, 4 minutes, and 5 minutes with ultrasonic agitation power of 500 W and an ultrasonic agitation frequency of 20 kHz to obtain three titanium dioxide dispersed solutions, and respectively testing the average particle size of the titanium dioxide particles in the three titanium dioxide dispersed solutions to get the test results shown in table 1 below;

(v) respectively mixing the three titanium dioxide dispersed solutions obtained by the different ultrasonic agitation times with the papermaking coating to obtain three equal mass antibacterial coatings, wherein in each antibacterial coating, the mass percentage of the titanium dioxide is 5% of the mass of the antibacterial coating; and (vi) employing three paper substrates made in step (ii), employing the three antibacterial coatings to respectively form antibacterial coating layers on the external surface of the three paper substrates to obtain three antibacterial papers, and employing an electron microscope to detect the superficial and cross-sectional structures formed on the external surfaces of the three antibacterial papers. The results are shown in FIGS. 4A~6B.

PRESENT DISCLOSED EXAMPLE

Figure 7A:
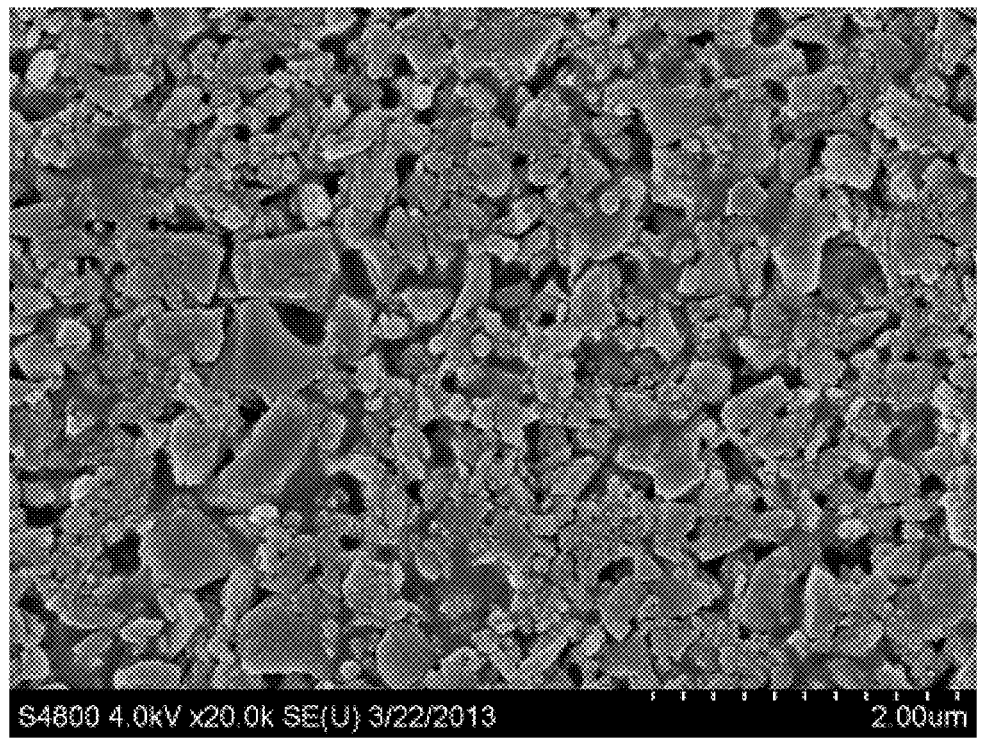
FIG. 7A and FIG. 7B respectively shows superficial and cross-sectional electron micrographs of an antibacterial coating layer formed by an antibacterial coating prepared by mechanical stirring with a speed of 5000 rpm and by ultrasonic agitation for 3 mins in a comparative example 3 of the present disclosure.
Figure 7B:
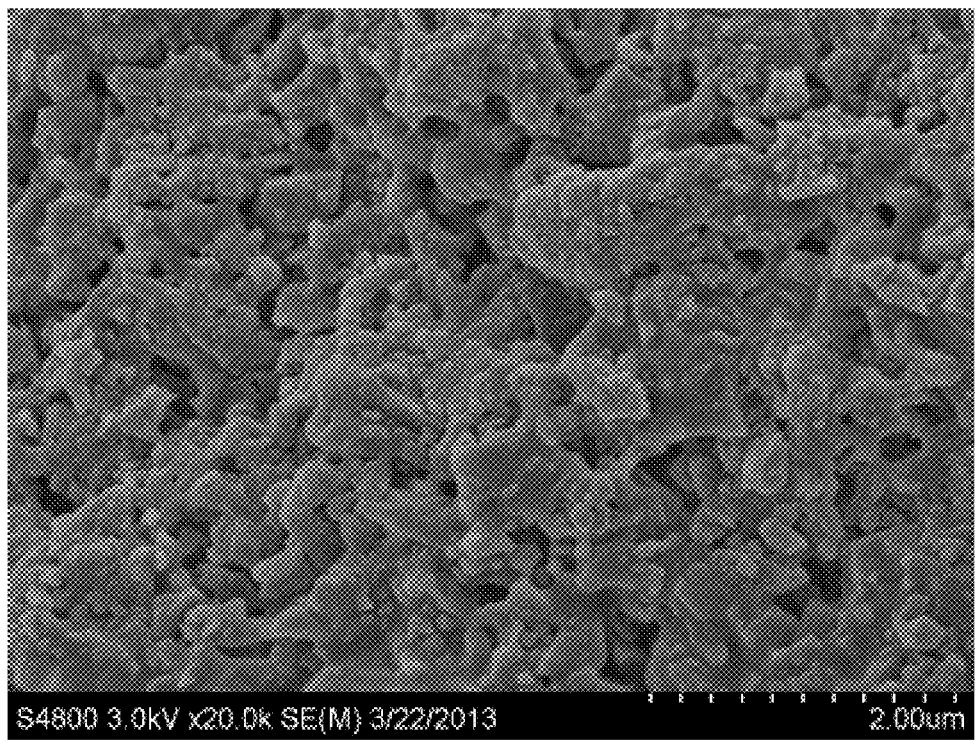

According to the present disclosure, during the process of preparing an antibacterial coating, firstly, the mechanical stirring method is employed to beat and break up the titanium dioxide finished product supplied by the titanium dioxide supplier. Then, the ultrasonic agitation method is employed to further beat and break up the titanium dioxide particles. Lastly, the antibacterial coating is employed to form an antibacterial coating layer on the external surface of a paper substrate to prepare an antibacterial paper. The specific steps include the following:

(i) preparing a papermaking pulp employing the following processes in this order: beating pulp, screening the pulp, cleaning the pulp, floating the pulp, heat-dispersing the pulp, bleaching the pulp, and refining the pulp;

(ii) employing the papermaking pulp to make the paper substrates;

(iii) preparing a papermaking coating;

(iv) preparing a nanometer-sized titanium dioxide dispersed solution according to the following steps: (a) adding NaOH into water to adjust the pH value of the water to 9, adding a dispersant into the water with a mass percentage of the dispersant being 0.3% of the mass of the titanium dioxide to be added, and stirring the water containing the dispersant with a rotational speed of 500 rpm to obtain a dispersant solution; (b) adding nano-treated titanium dioxide particles into the dispersant solution to obtain a mixed solution, wherein a mass percentage of the titanium dioxide particles in the mixed solution is 20% of the mass of the mixed solution; (c) employing three equal mass mixed solution samples from the mixed solution, and respectively mechanical stirring the three mixed solution samples for 30 minutes with rotational speeds of 5000 rpm, 6000 rpm, and 7000 rpm to obtain three titanium dioxide dispersed solutions; and (d) under the condition of ultrasonic agitation power being 500 W and ultrasonic agitation frequency being 20 kHz, employing ultrasonic agitation to stir the titanium dioxide dispersed solution obtained with the rotational speed of 5000 rpm for 3 minutes, stir the titanium dioxide dispersed solution obtained with the rotational speed of 6000 rpm for 4 minutes, and stir the titanium dioxide dispersed solution obtained with the rotational speed of 7000 rpm for 5 minutes, to obtain three nanometer-sized titanium dioxide dispersed solutions, and respectively testing the average particle size of the titanium dioxide particles in the three nanometer-sized titanium dioxide dispersed solutions to get the test results shown in table 1 below;

(v) mixing the nanometer-sized titanium dioxide dispersed solution prepared under the conditions of the mechanical stirring speed being 5000 rpm and the ultrasonic agitation time being 3 minutes with the papermaking coating to obtain an antibacterial coating, wherein the mass percentage of the nanometer-sized titanium dioxide in the antibacterial coating is 5% of the mass of the antibacterial coating; and (vi) employing a paper substrate made in step (ii), and employing the antibacterial coating obtained in step (v) to form an antibacterial coating layer on the external surface of the paper substrate and obtain an antibacterial paper, and employing an electron microscope to detect the superficial and cross-sectional structures of the antibacterial coating layer formed on the external surface of the antibacterial paper. The results are shown in FIG. 7A and FIG. 7B.

Results Part 1: The Distribution of the Average Particle Sizes

The average particle sizes of the titanium dioxide particles respectively obtained by the different dispersing methods are shown in table 1 below, wherein the titanium dioxide product shown in table 1 is the nano-treated titanium dioxide particles.

TABLE 1

| | titanium dioxide finished product | comparative example 1 mechanical stirring | | | comparative example 2 ultrasonic agitation | | | present disclosed example mechanical stirring + ultrasonic agitation | | |
|---|---|---|---|---|---|---|---|---|---|---|
| | | 5000 rpm | 6000 rpm | 7000 rpm | 3 min | 4 min | 5 min | 5000 rpm + 3 min | 6000 rpm + 4 min | 7000 rpm + 5 min |
| the average particle size | 1092 nm | 624 nm | 541 nm | 427 nm | 409 nm | 327 nm | 243 nm | 91 nm | 90.97 nm | 90.58 nm |

It can be clearly seen from table 1 that the average particle size of the titanium dioxide particles obtained by the dispersing method of the present disclosed example are much closer to nanometer level (e.g. the range from >0 to 100 nm) than the average particle size of the titanium dioxide product and the titanium dioxide particles obtained by the common dispersing method employed in each of comparative examples 1 and 2.

As described above in the Related Art section of this disclosure, the antibacterial capability of nanometer-sized titanium dioxide particles depends on the average size of the titanium dioxide particles. The smaller the average particle size of the titanium dioxide particles is, the better the antibacterial efficiency of the titanium dioxide particles is. Thus, it can be concluded that the antibacterial coating provided by the present disclosure has high antibacterial efficiency.

Results Part 2: The Dispersing Performance

By comparing the electron micrographs of the antibacterial coating layers coated on the external surface of the antibacterial papers respectively prepared by comparative example 1, comparative example 2, and the present disclosed example in FIGS. 1A~7B, the following conclusions can be drawn:

It can be seen from FIG. 1A to FIG. 3B that in the antibacterial coating layer formed by the antibacterial coating prepared by only employing mechanical stirring to beat and break up the titanium dioxide particles: (i) the titanium dioxide particles gradually uniformly disperse in the antibacterial coating layer as the stirring speed is increased; but (ii) the average particle size of the titanium dioxide particles is larger than 200 nanometers, and an obvious aggregation of the titanium dioxide particles exists.

FIGS. 4A~6B demonstrate that in the antibacterial coating layer formed by the antibacterial coating prepared by only employing ultrasonic agitation to beat and break up the titanium dioxide particles: (i) the particle size is smaller when the ultrasonic agitation time is 3 minutes, but a serious aggregation of the titanium dioxide particles exists; and (ii) the titanium dioxide particles gradually uniformly disperse in the antibacterial coating layer as the ultrasonic agitation time is increased, but the average particle size of the titanium dioxide particles gradually becomes larger.

As shown in FIG. 7A and FIG. 7B, the nanometer-sized titanium dioxide particles uniformly disperse in the antibacterial coating layer formed by the antibacterial coating prepared by the method of the present disclosed example. In addition, the average particle size of the titanium dioxide particles obtained by the dispersing method of the present disclosure is much less than the average particle size of the titanium dioxide particles obtained by the dispersing method of only employing mechanical stirring used in comparative example 1, and much less than the average particle size of the titanium dioxide particles obtained by the dispersing method of only employing ultrasonic agitation used in comparative example 2.

Thus, comparing the results of the electron micrographs shown in FIGS. 1A~7B, the titanium dioxide particles obtained by the dispersing method of the present disclosure and distributed in the antibacterial coating layer have a smaller size and disperse more uniformly.

Results Part 3: The Antibacterial Capability and the Printing Performance

In this embodiment, the antibacterial capability of the antibacterial paper is characterized with the antibacterial efficiency tested according to Chinese standard GB/T 21866-2008. The general testing method of the antibacterial efficiency includes the following steps: (i) inoculating quantitative bacteria in the antibacterial coating layer of antibacterial paper to be tested; (ii) making the bacteria uniformly distribute on the surface of the antibacterial coating layer by sticking a filter membrane on the surface of the antibacterial coating layer; and (iii) culturing the bacteria for about 24~48 hours, then testing the live bacteria numbers on the surface of the antibacterial coating layer. The higher the antibacterial efficiency is, the better the antibacterial capability is.

The printing performance of the antibacterial paper may be tested by the ink absorptivity of the antibacterial coating layer, the ink drying speed of the antibacterial coating layer, and the dispersible uniformity of the titanium dioxide particles in the antibacterial coating layer.

The value of the ink absorptivity is tested according to Chinese standard GB12911-1991. In this embodiment, the formula for approximately calculating the ink absorptivity is represented by the following equation $$\frac{R_0 - R_1}{R_0} * 100\%,$$

wherein $R_0$ represents the light reflection factor of the antibacterial coating layer before absorbing ink, and $R_1$ represents the light reflection factor of the antibacterial coating layer after absorbing ink. The higher the ink absorptivity is, the better the printing performance is.

The ink drying speed of the antibacterial coating layer surface is tested by the following steps: (i) employing a transfer paper to transfer the ink coated on the surface of the antibacterial paper to the surface of the transfer paper; and (ii) testing the ink density of the ink transferred on the surface of the transfer paper to evaluate the ink drying speed of the antibacterial coating layer surface. The higher the ink density of the ink transferred on the surface of the transfer paper is, the lower the ink drying speed of the antibacterial coating layer is, and the poorer the printing performance of the antibacterial paper is.

The results of the antibacterial capability and the printing performance of the antibacterial paper prepared by the different dispersing methods are summarized in table 2 below.

Compared to the prior art, the process of making the antibacterial coating, the process of making the antibacterial paper, and the antibacterial paper that are provided by the present disclosure have the following advantages: (i) the average particle size of the titanium dioxide particles in the antibacterial coating is less than or equal to 200 nm, which fully employs the antibacterial capability of the nanometer-sized titanium dioxide particles and makes the antibacterial efficiency of the antibacterial paper greater than 99%; and (ii) the good dispersible uniformity of the titanium dioxide particles in the antibacterial coating layer of the antibacterial paper makes the antibacterial coating layer have good printing performance. Thus, the antibacterial paper provided by the present disclosure not only has good antibacterial capability, but also has good printing performance.

It is to be further understood that even though numerous characteristics and advantages of the present embodiments have been set forth in the foregoing description, together with details of the structures and functions of the embodiments, the disclosure is illustrative only, and changes may be made in detail, especially in matters of arrangement of parts within the principles of the disclosure to the full extent indicated by the broad general meaning of the terms in which the appended claims are expressed.

TABLE 2

| | dispersing method | | | | | | | | |
|---|---|---|---|---|---|---|---|---|---|
| | comparative example 1 | | | comparative example 2 | | | present disclosed example mechanical stirring + ultrasonic agitation | | |
| | mechanical stirring | | | | | | 5000 | 6000 | 7000 |
| performances | 5000 rpm | 6000 rpm | 7000 rpm | ultrasonic agitation | | | rpm + | rpm + | rpm + |
| parameter | | | | 3 min | 4 min | 5 min | 3 min | 4 min | 5 min |
| antibacterial efficiency % | 93.28 | 94.33 | 95.14 | 96.18 | 97.01 | 98.45 | 99.99 | 99.99 | 99.99 |
| ink drying speed  30 s | 0.49 | 0.48 | 0.47 | 0.46 | 0.45 | 0.44 | 0.43 | 0.43 | 0.42 |
| 60 s | 0.45 | 0.44 | 0.43 | 0.43 | 0.42 | 0.41 | 0.36 | 0.35 | 0.35 |
| 90 s | 0.40 | 0.39 | 0.39 | 0.38 | 0.37 | 0.36 | 0.33 | 0.32 | 0.32 |
| 120 s | 0.35 | 0.34 | 0.33 | 0.32 | 0.29 | 0.26 | 0.24 | 0.24 | 0.24 |
| ink absorptivity | 21.60 | 21.65 | 21.74 | 21.85 | 21.88 | 22.30 | 22.90 | 22.95 | 23.02 |

From the data shown in table 2, it can be seen that: (i) with regard to antibacterial efficiency, the antibacterial efficiency of the antibacterial paper prepared by the method of the present disclosure is much higher than the antibacterial efficiency of the antibacterial paper prepared by the common methods, which further verifies that the antibacterial paper using the antibacterial coating prepared by the method of the present disclosure has good antibacterial capability; and (ii) with regard to printing performance, compared to the antibacterial paper prepared by the common methods, the ink density of the ink transferred on the surface of the transfer paper corresponding with the antibacterial paper prepared by the method of the present disclosure is lowest, and the ink absorptivity of the antibacterial paper prepared by the method of the present disclosure is highest. Therefore, the printing performance of the antibacterial paper prepared by the method of the present disclosure is best.

It can be plainly seen according to the data shown in table 2 that, compared to the antibacterial paper prepared by the common dispersing methods, the antibacterial paper provided by the method of the present disclosure not only has good antibacterial capability, but also has good printing performance.

What is claimed is:

1. A method of making an antibacterial coating, the method comprising:
    preparing a mixed solution containing titanium dioxide particles and a dispersant;
    beating and breaking up the titanium dioxide particles in the mixed solution by mechanical stirring to prepare a preliminary titanium dioxide dispersed solution;
    further beating and breaking up the titanium dioxide particles in the preliminary titanium dioxide dispersed solution by ultrasonic agitation to prepare a titanium dioxide dispersed solution with an average particle size of the titanium dioxide particles being less than or equal to 200 nanometers; and
    mixing the titanium dioxide dispersed solution with papermaking coating to prepare an antibacterial coating with the titanium dioxide particles uniformly dispersed therein, the mass percentage of the titanium dioxide particles in the antibacterial coating being more than or equal to 5% of the mass of the antibacterial coating.

2. The method of claim 1, wherein the stirring speed of the mechanical stirring is in the range of from 5000~7000 revolutions per minute, and the stirring time of the mechanical stirring is in the range of from 30~60 minutes.

3. The method of claim 1, wherein the power of the ultrasonic agitation is 500 W, the frequency of the ultrasonic agitation is in the range of from 10~100 kHz, and the time of ultrasonic agitation is in the range of from 3~5 minutes.

4. The method of claim 1, wherein the mass percentage of the titanium dioxide particles contained in the antibacterial coating is in the range of from 5%~15% of the mass of the antibacterial coating.

5. The method of claim 1, wherein the mass percentage of the dispersant contained in the mixed solution is in the range of from 0.3%~0.5% of the mass percentage of the titanium dioxide particles contained in the mixed solution.

6. The method of claim 1, further comprising adjusting the pH value of the titanium dioxide dispersed solution to keep consistent with the pH value of the papermaking coating before mixing the nanometer titanium dioxide dispersed solution with the papermaking coating.

7. A method of making an antibacterial paper, the method comprising:
    providing a paper substrate;
    preparing an antibacterial coating according to the method of claim 1; and
    employing the antibacterial coating to form an antibacterial coating layer on at least one external surface of the paper substrate.

8. The method of claim 7, wherein the paper substrate includes a surface layer, a sandwich layer, and a bottom layer, the antibacterial coating layer coats on the external surface of the surface layer and/or the bottom layer.

* * * * *